US00PP29646P3

(12) United States Plant Patent
Randag

(10) Patent No.: US PP29,646 P3
(45) Date of Patent: Sep. 4, 2018

(54) CALLA LILY PLANT NAMED 'SANTIAGO'

(50) Latin Name: *Zantedeschia sprengeri*
Varietal Denomination: Santiago

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 44 days.

(21) Appl. No.: 15/530,233

(22) Filed: Dec. 14, 2016

(65) Prior Publication Data

US 2017/0181362 P1 Jun. 22, 2017

Related U.S. Application Data

(60) Provisional application No. 62/386,953, filed on Dec. 17, 2015.

(51) Int. Cl.
*A01H 5/02* (2018.01)

(52) U.S. Cl.
USPC ..... Plt./490

(58) Field of Classification Search
USPC ..... Plt./263.1, 490
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

'Santiago' is a new variety of calla lily having inflorescences with a purple/red-colored spathe that produces 5-25 inflorescences per tuber. The inflorescence stems are about 19-40 cm in height, and the leaves are green with whitish spots and have a leathery texture.

3 Drawing Sheets

Botanical classification: *Zantedeschia sprengeri*.
Varietal denomination: 'SANTIAGO'.

BACKGROUND OF THE NEW PLANT

The present invention comprises a new and distinct cultivar of calla lily, botanically known as *Zantedeschia sprengeri* and hereinafter referred to by the cultivar name 'Santiago'.

'Santiago' is a product of a planned breeding program which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* variety 'Allure' (female parent, unpatented) with a *Zantedeschia sprengeri* selection referred to as Z030530-640 (male parent, unpatented). 'Santiago' was selected in 2012 by the inventor in 't Zand, The Netherlands as one flowering plant within the progeny of the stated cross.

The first act of asexual reproduction of 'Santiago' by tissue culture was performed by the inventor in September of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots at 12-14 weeks after planting in 't Zand, The Netherlands under greenhouse conditions, which approximate those generally used in horticultural practice. Color references are made to The 2001

R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Santiago' which, in combination, distinguish this calla lily as a new and distinct cultivar:

1. Purple/red-colored spathes;
2. Compact plant architecture; and
3. High inflorescence production.

Further, when compared to calla lily plant named 'Majestic Star' (U.S. Plant Pat. No. 18,110), the upper surface spathe color of 'Majestic Star' is listed between Red Group RHS 53A and Red-Purple Group RHS 60A, and the lower surface spathe color of 'Majestic Star' is listed between Red-Purple Group RHS 60B and RHS 60C. However, the upper and lower surface spathe color of 'Santiago' varies between Red-Purple Group RHS 59A and 60B.

Table 1 provides differences of 'Santiago' to its parents, *Zantedeschia sprengeri* variety 'Allure' and selection Z030530-640.

TABLE 1

| 'Santiago' | Differences | |
|---|---|---|
| 'Allure' | Spathe color | Varies between Red-Purple Group RHS 59A and 59B |
| | Plant height | 20-25 cm |
| Z030530-640 | Spathe color | Varies between Red-Purple Group RHS 59C and 60A |
| | Plant height | 35-50 cm |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

The Plant

Figure 1:
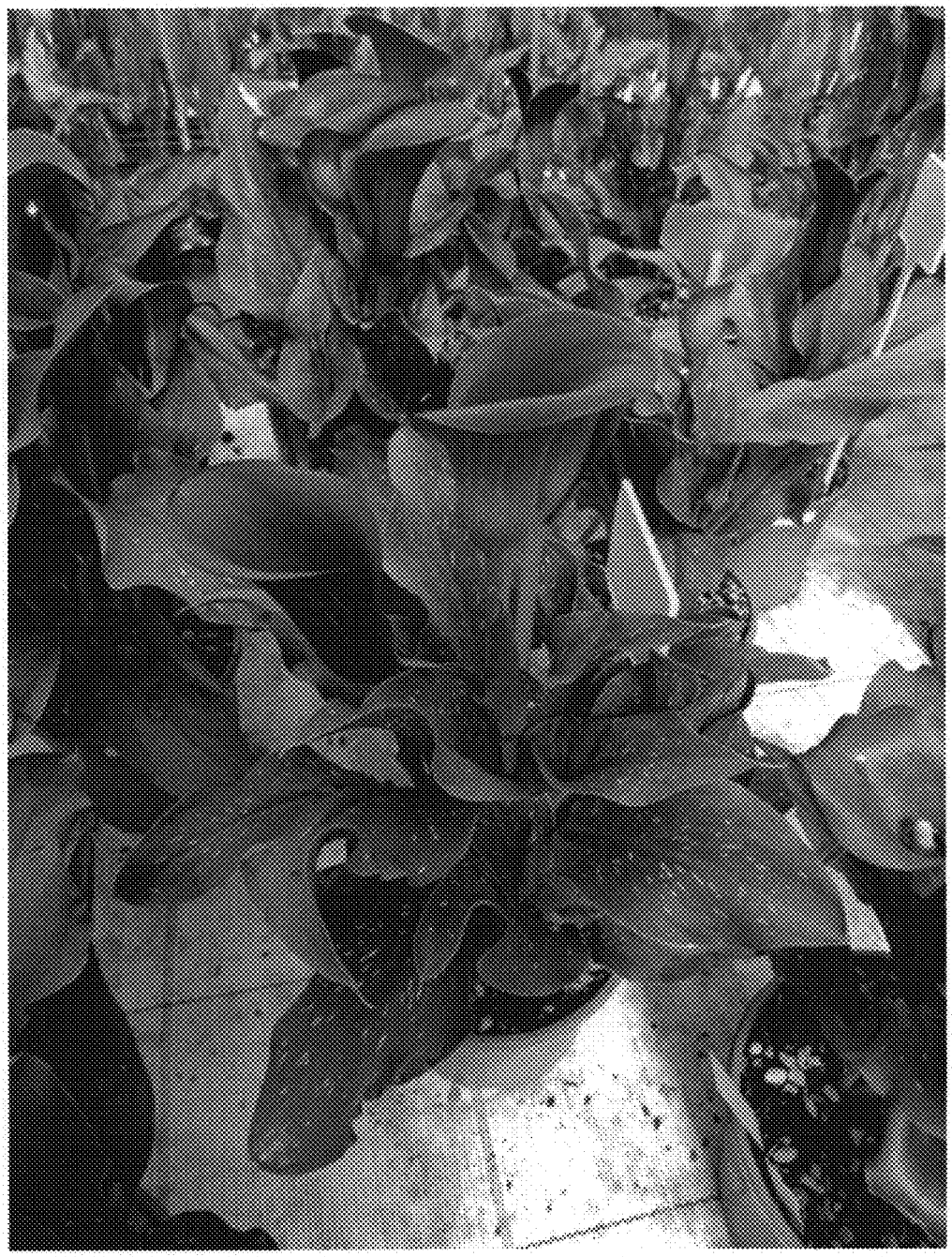
FIG. 1 is a photograph of a top view of a potted plant of the new variety.
Figure 2:
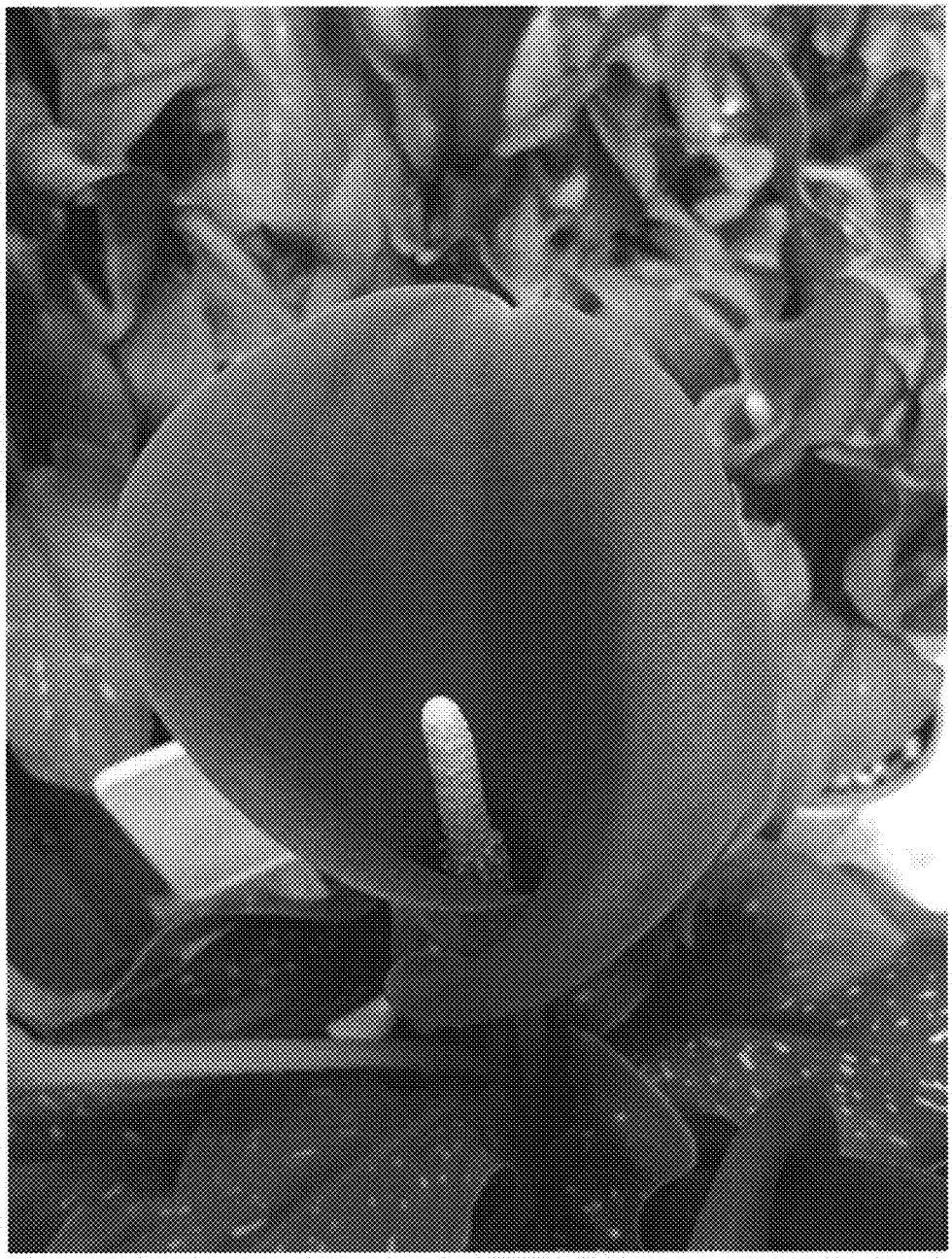
FIG. 2 is a photograph of a close-up view of the new variety.
Figure 3:
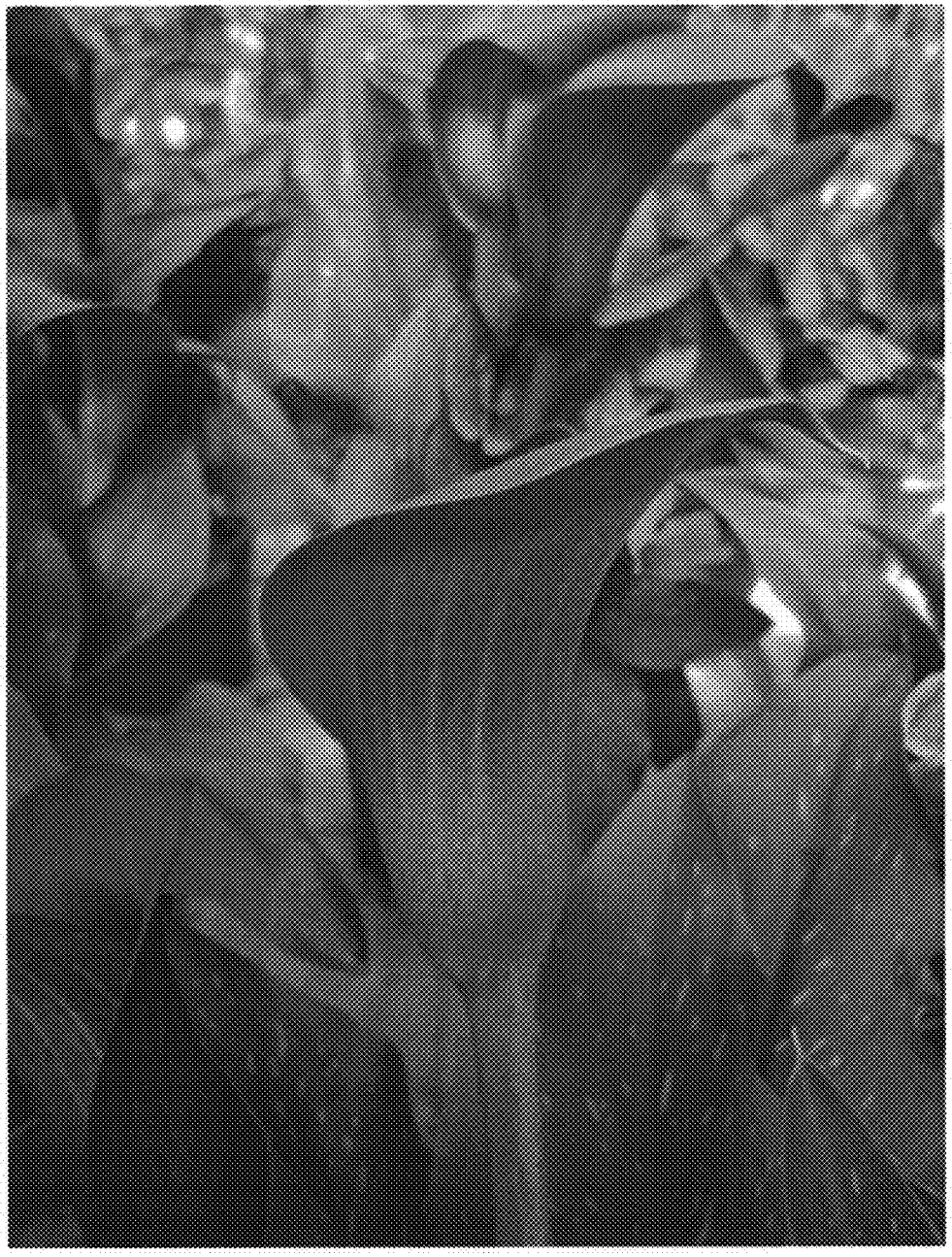
FIG. 3 is a photograph of a side view of the new variety.

Size:
- *Height of the leaf canopy above the soil.*—15-35 cm.
- *Height of top of inflorescence above the soil.*—19-40 cm.
- *Diameter.*—8-12 cm.

Form: Semi-spreading.

Number of inflorescences per tuber:
- *Size* 14-16 *cm in diameter.*—5-7 inflorescences.
- *Size* 16-18 *cm in diameter.*—8-11 inflorescences.
- *Size* 18-20 *cm in diameter.*—10-12 inflorescences.
- *Size* 20-22 *cm in diameter.*—10-25 inflorescences.

Branches:
- *Number.*—From 3-10.
- *Color.*—Between Yellow-Green Group RHS 146A and 146C.

Leaves:
- *Size.*—Width: 3.5-12.5 cm. Length: 10-23 cm.
- *Number per plant.*—18-24.
- *Shape.*—Lanceolate.
- *Color.*—Upper surface: Green Group RHS 137A to 137B, with transparent White Group RHS 155A and N155A spots. Lower surface: Green Group RHS 137A to 137B, with transparent White Group RHS 155A and N155A spots.
- *Apex.*—Apiculate.
- *Base.*—Attenuate.
- *Margin.*—Undulate; having a color of Green Group RHS 141B to 141C.
- *Veins.*—Configuration: Pinnate. Color: Green Group RHS 141A to 141C.
- *Surface quality.*—Leathery.
- *Petiole.*—Length: 4-15 cm. Average diameter: 12 mm. Color: The base is White Group RHS 155A, and the upper part is Yellow-Green Group RHS 144A to 144C.

Roots:
- *Color.*—White.
- *Branching.*—Similar to other *Zantedeschia* varieties.

The Inflorescence and Seeds

Spathe:
- *Size.*—Length (measured from base opening to tip): 5-10 cm. Width: 3-7 cm. Height: 6-11 cm.
- *Color.*—Upper surface: Varies between Red-Purple Group RHS 59A and 60B. Lower surface: Varies between Red-Purple Group RHS 59A and 60B.
- *Vein color.*—Red-Purple Group RHS 59A.
- *Shape.*—Funnel.
- *Apex.*—Apiculate.
- *Base.*—Obtuse.
- *Texture.*—Smooth (upper and lower surfaces).

Spadix:
- *Size.*—Length: 20-50 mm. Diameter: 3-5 mm.
- *Color.*—Varies between Yellow-Orange Group RHS 17A and 21B.
- *Position relative to spathe.*—Upright.

Peduncle:
- *Size.*—Length: 13-29 cm. Diameter: 3-9 mm.
- *Color.*—The upper part is between Green Group RHS 143A to 143C, and the lower part is Green-White Group RHS 157C.
- *Texture.*—Smooth.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.
- *Anther.*—Shape: Round. Length: Less than 1 mm. Color: Between Yellow-Orange Group RHS 17A and 21B.
- *Filament.*—Length: Less than 1 mm. Color: Between White Group RHS 155A and 155B.
- *Pistil.*—Number: 15 to 30. Length beyond perianth: About 1 mm.
- *Stigma.*—Shape: Round. Size: Less than 1 mm.
- *Style.*—Length: Less than 1 mm. Color: Between Greyed-Purple Group RHS 186A and 186B.
- *Ovaries.*—Texture: Smooth. Length: Between 1 to 10 mm. Width: Between 1 to 10 mm. Color: Top color is between Yellow-Orange Group RHS 17A and 21A, bottom color is from White Group RHS 155B to Green-White Group RHS 157C.

Seeds:
- *Length.*—4-7 mm.
- *Width.*—3-6 mm.
- *Color.*—Between Yellow-Green Group RHS 150A and 151A.
- *Amount.*—Between 1-55.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Santiago' as herein described and illustrated.

* * * * *